US006998181B2

(12) United States Patent
O'Dell et al.

(10) Patent No.: US 6,998,181 B2
(45) Date of Patent: Feb. 14, 2006

(54) POLYMER AND USES THEREOF

(75) Inventors: Richard O'Dell, Taufkirchen (DE); Carl Robert Towns, Stansted (GB); Mary Joyce McKiernan, Cambridgeshire (GB)

(73) Assignee: Cambridge Display Technology Limited, Cambridge (GB)

( * ) Notice: Subject to any disclaimer, the term of this patent is extended or adjusted under 35 U.S.C. 154(b) by 0 days.

(21) Appl. No.: 10/381,544

(22) PCT Filed: Sep. 25, 2001

(86) PCT No.: PCT/GB01/04281

§ 371 (c)(1),
(2), (4) Date: Jun. 23, 2003

(87) PCT Pub. No.: WO02/26859

PCT Pub. Date: Apr. 4, 2002

(65) Prior Publication Data

US 2004/0024161 A1 Feb. 5, 2004

Related U.S. Application Data

(60) Provisional application No. 60/265,018, filed on Jan. 30, 2001.

(30) Foreign Application Priority Data

Sep. 26, 2000 (GB) .............................................. 0023539
Nov. 17, 2000 (GB) .............................................. 0028126

(51) Int. Cl.
*B32B 27/28* (2006.01)
*H05B 33/14* (2006.01)

(52) U.S. Cl. ............. 428/690; 252/301.16; 252/301.32; 428/917; 528/397; 528/422

(58) Field of Classification Search ................. 528/397, 528/422; 428/690
See application file for complete search history.

(56) References Cited

U.S. PATENT DOCUMENTS

| 5,728,801 A | 3/1998 | Wu et al. | .................... 528/422 |
|---|---|---|---|
| 5,777,070 A | 7/1998 | Inbasekaran et al. | ....... 528/394 |
| 5,830,980 A | 11/1998 | Anzai et al. | ................. 528/272 |
| 6,329,086 B1 | 12/2001 | Shi et al. | ..................... 428/690 |
| 6,414,104 B1 * | 7/2002 | Pei | .............................. 528/86 |
| 6,723,828 B2 * | 4/2004 | Pei | ............................. 528/422 |

FOREIGN PATENT DOCUMENTS

| JP | 11-34457 | 5/1989 |
|---|---|---|
| JP | 2000-072722 | 3/2000 |
| WO | WO 90/13148 | 11/1990 |
| WO | WO 00/53656 | 9/2000 |
| WO | WO 00/55927 | 9/2000 |

OTHER PUBLICATIONS

"Organic Electroluminescent Diodes", Tang et al., Appl. Phys, Lett. 51 (12), Sep. 21, 1987, pp. 913–915.
"Imine–Bridged Planar Poly(p–phenylene) Derivatives for Maximization of Extended π–Conjugation. The Common Intermediate Approach", Lamba et al., J. Am. Chem. Soc., 116, 1994, pp. 11723–11736.
"Effect of Layered Structures on the Location of Emissive Regions in Organic Electroluminescent Devices", Aminaka et al., J. Appl. Phys. 79 (11), Jun. 1, 1996, pp. 8808–8815.
"Structures and Photophysical Properties of Model Compounds for Arylethylene Disilylene Polymers", Douglas et al., Macromolecules, 31, Jan. 31, 1998, pp. 1093–1098.
International Search Report in PCT/GB01/04281 dated Feb. 11, 2002.
International Preliminary Examination Report in PCT/GB01/04281 dated Jun. 17, 2002.

* cited by examiner

*Primary Examiner*—Randy Gulakowski
*Assistant Examiner*—Marc S Zimmer
(74) *Attorney, Agent, or Firm*—Marshall, Gerstein & Borun LLP

(57) ABSTRACT

A polymer including a region having a conjugated backbone capable of transporting negative charge carriers, which region includes a plurality of repeat units each including a core group which includes an [Ar'] group substituted with at least one pendant group X and the [Ar'] groups form at least a part of the backbone, wherein each Ar' includes an aromatic or heteroaromatic group and each X includes $NAr_2$ in which each Ar is the same or different and independently includes a substituted or unsubstituted aromatic or heteroaromatic group and N is conjugated with the backbone.

27 Claims, 1 Drawing Sheet

POLYMER AND USES THEREOF

This is the U.S. national phase of International Application No. PCT/GB01/04281 filed Sep. 25, 2001, and claims the benefit under 35 U.S.C. § 119(e) of U.S. provisional patent application Ser. No. 60/265,018 filed Jan. 30, 2001, the entire disclosure of which is incorporated herein by reference.

The present invention relates to an organic polymer and uses thereof such as in an optical device.

A typical device for emitting light will comprise an anode electrode, a cathode electrode and a light-emissive layer located between the electrodes. Holes and electrons that are injected from the electrodes recombine radiatively in the light-emissive layer. Organic electroluminescent devices are known which employ an organic material for light-emission. For example, WO 90/13148 describes such a device comprising a semi-conductor layer comprising a polymer film which comprises at least one conjugated polymer situated between electrodes. The polymer film in this case comprises a poly(para-phenylene vinylene) film which is capable of light emission when electrons and holes are injected therein.

Known device structures also may have an electron transport layer situated between the cathode and the light-emissive layer. This provides an intermediate energy level which helps the electrons injected from the cathode to reach the LUMO (lowest unoccupied molecular orbital) level of the material constituting the light-emissive layer. Suitably, the electron transporting layer has a LUMO energy level between the LUMO energy levels of the cathode and the light-emissive layer. A device including an electron transport layer is disclosed in, for example, J. App. Phys., 1996, 79(11), pg. 8808–8814 and references therein.

Similarly, known device structures also may have a hole transport layer situated between the anode and the light-emissive layer. Devices disclosed in Applied Physics Letters, 51, 913–915 (1987) consist of a hole transport layer of an aromatic diamine and an emissive layer of 8-hydroxyquinoline aluminium. ITO is used as the hole injecting electrode and a magnesium silver alloy as the electron injecting electrode.

Poly(arylamines) are disclosed in U.S. Pat. No. 5,728,801 as useful charge transport layers in light-emissing diodes. This document further discloses that triarylamines are used as charge transport materials, specifically positive charge transport materials, because they are easily oxidised to the corresponding radical cation. The usefulness of the possibility of using these polymers in film form is discussed in this document.

One disadvantage associated with multiple layer devices is that where the layers are deposited from solution it is difficult to avoid one layer being disrupted when the next is deposited. Problems can arise with voids or material trapped between the increased number of interlayer boundaries.

This problem has been addressed in the prior art. One solution has been to use a blend of at least two different materials in any given layer. For example, a blend could comprise one material for transporting positive charge carriers and a second material for transporting negative charge carriers. Such a blend is disclosed in WO99/48160. For example, this document discloses an emissive layer that is a three component mixture of F8(poly(2,7-(9,9-di-n-octylfluorene) mixed with F8BT(poly(2,7-(9,9-di-n-octylfluorene)-3,6-Benzothiadzole) in the ratio 19:1 and then that mixture is mixed with TFB(poly(2,7-(9,9-di-n-octylfluorene)-(1,4-phenylene-((4-secbutylphenyl)imino)-1,4-phenylene)) in the ratio 4:1.

A second proposed solution to this problem has been to provide a single material that is capable of transporting negative charge carriers and that also is capable of (a) transporting positive charge carriers and/or (b) accepting and combining positive and negative charge carriers to generate light. Such a material is known from PCT/GB00/00911. This document discloses an organic polymer having a plurality of regions along the length of the polymer backbone where each region has a bandgap that is distinct from the other regions so that the polymer is capable of performing more than one of the functions mentioned above. One polymer disclosed in this document is shown below:

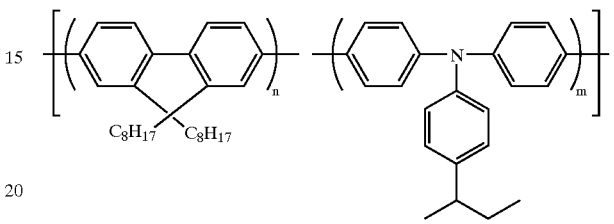

the ratio of n to m is about 10.

It can be seen that the backbone of the above polymer is not conjugated along its length because the nitrogen atoms in the polymer backbone act as nodes preventing full conjugation and hence, providing a barrier to and preventing efficient transport of negative charge carriers.

It is an aim of the present invention to provide an improved solution to the above problem. Accordingly, the present invention provides a polymer comprising a region having a conjugated backbone capable of transporting negative charge carriers, which region comprises a plurality of repeat units each comprising a core group which comprises an $-\!\!+\!\!Ar'\!\!+\!\!-$group substituted with at least one pendant group X and the $-\!\!+\!\!Ar'\!\!+\!\!-$groups form at least a part of the polymer backbone, wherein each Ar' comprises an aromatic or heteroaromatic group and each X comprises $NAr_2$ in which each Ar is the same or different and independently comprises a substituted or unsubstituted aromatic or heteroaromatic group and N is conjugated with the polymer backbone.

Figure 1:
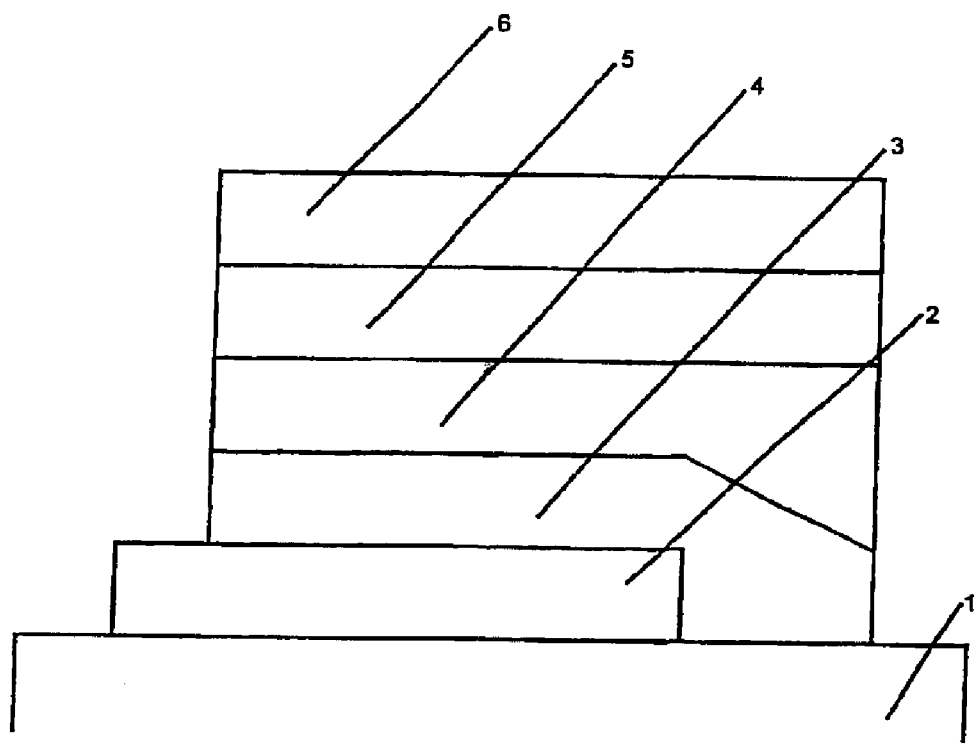
FIG. 1 shows an optical device structure including an emissive layer comprising a polymer capable of transporting negative charge carriers in accordance with the invention.

By conjugated backbone is meant a backbone which possesses a delocalised Π-electron system along its length; the delocalised Π-electron system confers semiconducting properties to the polymer and gives it the ability to support positive and negative charge carriers with high mobilities along the polymer chain.

The conjugated backbone contains no nodes which provide a barrier to negative charge transport. For the purposes of the present invention such a conjugated backbone may be defined as fully conjugated.

The present polymer preferably consists of a single 'region' or a plurality of 'regions' which perhaps may be separated by a node preventing full conjugation.

Preferably, the region additionally either is capable of transporting positive charge carriers in the polymer or is capable of combining positive and negative charge carriers in the polymer to generate light.

Where the region is capable of accepting and combining positive and negative charge carriers to generate light, it is believed that the polymers will be most useful in generating "blue" light.

In the defined region of the present polymer, there is no barrier to electron movement in the polymer backbone. Thus, the region is extremely efficient in transporting negative charge carriers. Furthermore, any holes residing on the nitrogen(s) in the NAr$_2$ group(s) are conjugated with the polymer backbone. In other words, the nitrogen(s) is conjugatively linked to the polymer backbone. This allows facile hole-electron combination in the present polymer as compared with the combination of a hole residing on a nitrogen pendant to the polymer backbone that is non-conjugated with the polymer backbone.

When the present polymer is used in an electroluminescent device, device efficiency is increased and material synthesis is minimised.

In a specific embodiment, the polymer backbone does not contain any nitrogen atoms.

The number of pendant groups X to Ar' is preferably 1 or 2. However, further pendant groups X from Ar' are not excluded. The number of possible pendant groups X predominantly is limited by steric effects.

In the present polymer, it is preferred that the each core group has formula:

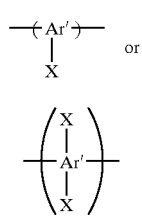

I or

II where X and X' are the same or different and each independently is as X is defined below.

It is further preferred in the present polymer, in some embodiments, that the region comprises two core groups linked in the polymer backbone by a direct covalent bond. Thus, for example, the region could comprise a group having formula:

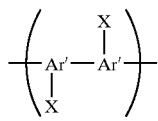

where each Ar' and each X is the same or different.

Preferably, X and X' are capable of transporting positive charge carriers in the polymer.

It is preferred in NAr$_2$ that each Ar comprises a substituted or unsubstituted aryl or heteroaryl group. More preferably, each Ar comprises at least one phenyl or pyridyl group. These groups are preferred for ease of synthesis.

It is envisaged that, usually, each Ar in NAr$_2$ will be the same.

Referring to Ar', it is preferred that Ar' comprises an aryl or heteroaryl group. This is to further facilitate electron transport along the polymer backbone. It is most preferable that Ar' comprises a phenyl group for this reason.

In one embodiment, Ar' does not comprise a fluorene group.

In a first aspect of the present invention, the core group has a formula:

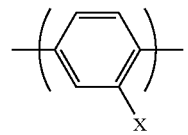

III

More preferably, the core group has a formula:

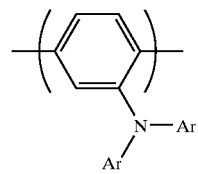

IV

Even more preferably, the core group has a formula:

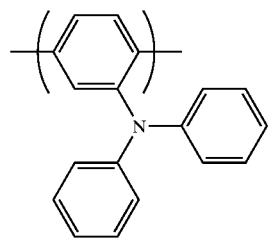

V

A polymer according to this aspect is envisaged to be extremely useful for transporting negative charge carriers and for accepting and combining positive and negative charge carriers to generate light. However, any polymer according to the present invention may have these properties. In general, it is preferred that where a polymer according to the present invention and particularly the defined region has the capability of accepting and combining positive and negative charge carriers to generate light, the polymer or region will be capable of generating light "blue" light, particularly having a wavelength in the range 410 nm to 650 nm, preferably about 460 nm.

In a second aspect of the present invention, the core group has a formula:

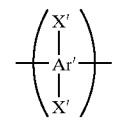

II

It is preferred that X and X' are ortho or para to one another. This enables very efficient transportation of holes within the defined region of the polymer.

According to this second aspect of the present invention, it is preferred that the core group has a formula:

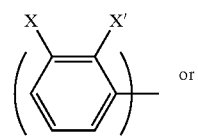

VI or

-continued

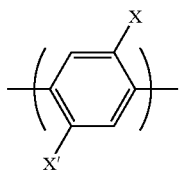
VII

More preferably, the core group has a formula:

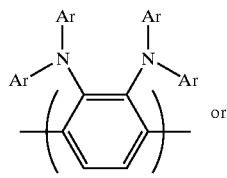
VIII or

IX

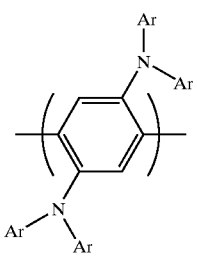

Even more preferably, the core group has a formula:

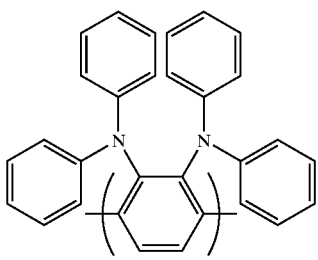
X

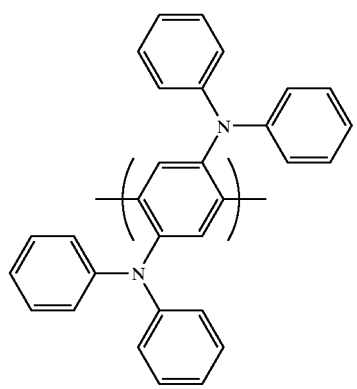
XI

It should be understood that the pendant phenyl groups shown in the above formulae may be substituted or unsubstituted. Possible substituents would include an alkyl, aryl, arylalkyl, alkylaryl, alkoxy, aryloxy, or haloalkyl group, in particular $CF_3$.

The present inventors have found that much improved hole transport in the defined region of the present polymer can be achieved when the core group is a bis(triaryl)amine, particularly a para-bis(triaryl)amine. Particularly the core group may have a formula:

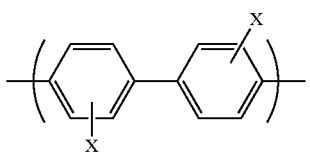
XII

For example:

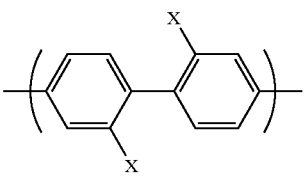
XIII

More preferably, for further improving hole transport in the polymer, the core group is ortho-bis(triaryl)amine and preferably has formula:

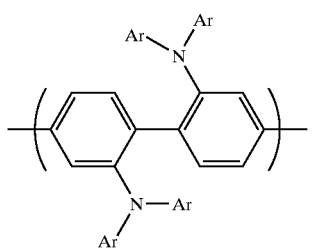
XIV

Arylamino substituted biphenyls (i.e. "amine" units) also are preferred.

Even more preferably, the core group has a formula (which is substituted or unsubstituted):

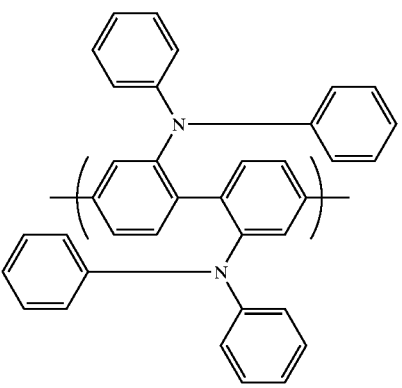
XV

In the present polymer, it is preferred that the repeat unit comprises one or more groups G in the polymer backbone in addition to the core group. Each G may be the same or different and each independently comprises a substituted or unsubstituted aromatic or heteroaromatic group.

Preferably, when the repeat unit comprises one or more G groups, the repeat unit will have a formula:

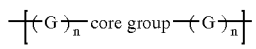

where 0≤n≤5. Preferably, n=1 or 2.

For the same reasons as discussed above in relation to Ar', it is preferred that each G independently comprises a substituted or unsubstituted aryl or heteroaryl group. Preferred G groups include thienyl, phenyl, pyridyl, furan. These groups contribute to the extent of conjugation in the defined region and, thus, can be used to at least partially control the bandgap of the polymer and to facilitate electron transport along the polymer backbone. More preferable G groups include thienyl and phenyl groups.

Where the repeat unit or region comprises one or more G groups, a preferred repeat unit or region may comprise a group having a formula:

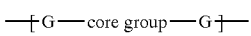

i.e. n=1 in formula XVI for example

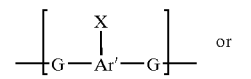

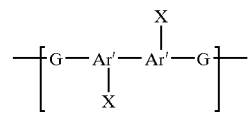

Preferably, in formula XVIII or formula XIX, Ar' and X are as defined in any preferred embodiment described above.

In formulae XVII to XIX above, it is preferred that each G is a heteroaromatic group, preferably a substituted or unsubstituted thiophene group. Preferred substituent groups on G include alkyl, alkoxy, aryl and heteroaryl groups.

Polymers where a repeat unit or region comprises a group as defined in one of formulae XVII to XIX above, have been found to emit light efficiently when used as an optical device. The introduction of the G groups into these polymers has been found to lower the ionisation potential of the polymer By appropriate selection of Ar', X, G and any optional substituents, the bandgap and thus the transport properties and emission colour of the polymer may be tuned.

Accordingly, more preferred groups that optionally may be further substituted have formulae:

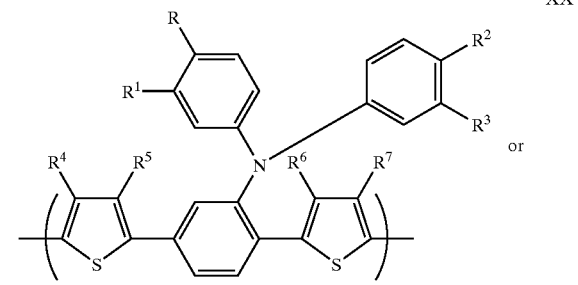

where R to $R^{11}$ may be the same or different and each is selected independently from the group consisting of hydrogen; or substituted or unsubstituted alkyl, perfluoroalkyl, alkylaryl, arylalkyl, heteroaryl, aryl, alkoxy, thioalkyl or cyano groups. These are preferred because they are suitable for helping to select the HOMO level and/or for improving solubility of the polymer More preferably R to $R^{11}$ independently are selected from the group consisting of hydrogen, substituted or unsubstituted alkyl, aryl and heteroaryl. In this regard ? groups are preferred.

An example of a polymer according to the present invention where the repeat unit comprises 2 G groups where G is Ar is as shown below:

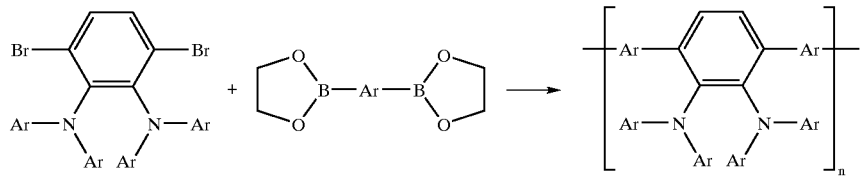

-continued
Scheme 2.
Metal catalysed polymerisation

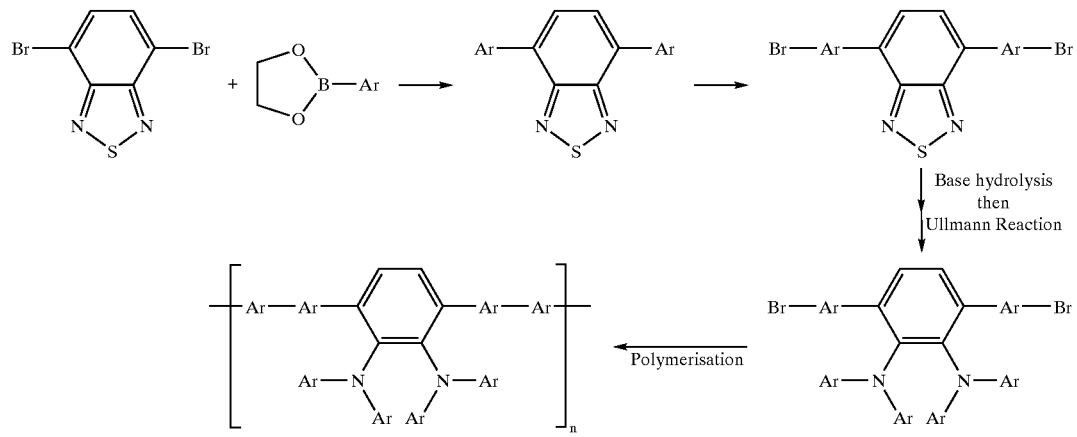

In the above scheme the ortho-bis(triaryl)amine is further derivatised into a trimer unit via a metal catalysed coupling of an aromatic bis-boronic ester with dibromo-benzothiadiazole.

While a polymer according to the present invention includes any polymer such as a homopolymer, copolymer, terpolymer or oligomer, it is preferred that the present polymer comprises a copolymer. In this regard, a copolymer may be defined to have been made from two or more different monomers. If the copolymer is a regular alternating copolymer, the polymer may be defined to have only one repeat unit. In other words, an AB regular alternating polymer which has been made from monomers A and B may be defined to have an AB repeat unit.

Preferred copolymers are 1:1 copolymers as shown in the worked Example.

A further preferred copolymer has the formula:

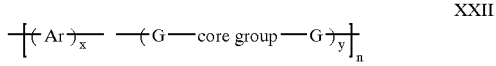
XXII where $x+y=1$, and $x \geq 0.3$ and $y \leq 0.7$; preferably $0.4 \leq x \leq 0.98$ and $0.02 \leq y \leq 0.6$; the core group is as defined in any embodiment above; $2 \leq n \leq 1000$; and the copolymer may be regular alternating, block or random.

Particularly preferred co-polymers have a formula:

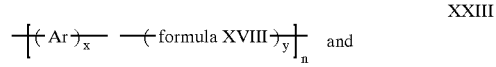
XXIII and

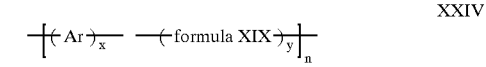
XXIV where x and y and n are as defined in relation to formula XXII. Formulae XVIII and XIX may be defined further in formulae XXIII and XXIV as shown in formulae XX and XXI, respectively. Preferred polymers having formulae XXIII and XXIV have x=y=0.5 (i.e. 1:1 copolymers).

In the present invention, where the present polymer is a copolymer, a preferred comonomer comprises fluorene. An exemplified polymer according to the present invention is shown below:

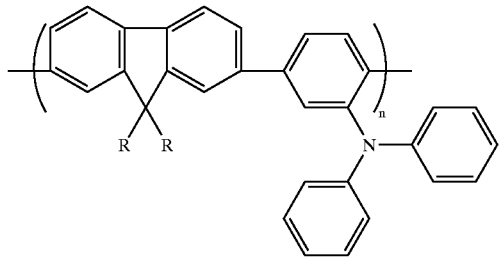

where $2 \leq n \leq 1000$ and R is any suitable substituent group such as alkyl, alkoxy, aryl, arylalkyl, alkylaryl or the like. Preferably, n is about 100.

For any polymer according to the present invention, it is preferred that the degree of polymerisation is in the range of from 2 to 1000, preferably in the range 20 to 200, even more preferably about 100.

Two further polymers according to the present invention are shown below:

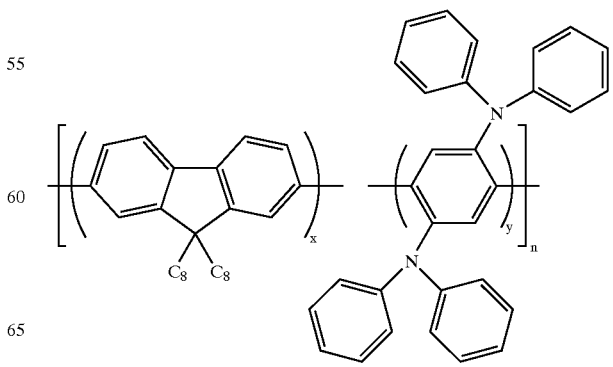

-continued

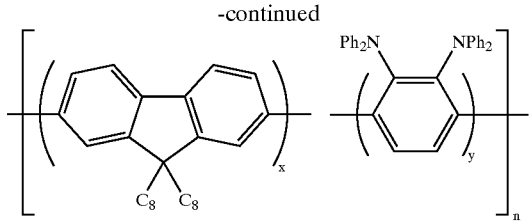

where, preferably, x≧0.5, y≦0.5 and n is as defined above. Particularly preferred ratios of x:y are 1:1 and approximately 90:10. In the above polymers, for ease of preparation, the fluorene groups would be provided as comonomers together with one of the monomers according to the present invention shown below:

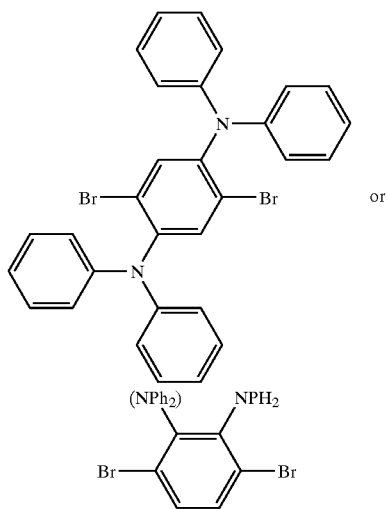

Suitably, the comonomers containing fluorene would contain two reactive boron derivative groups for reaction under suitable polymerisations conditions with the bromine reactive groups on the monomers according to the present invention.

Generally, several different polymerisation methods are known which may be used to manufacture polymers in accordance with the present invention.

One suitable method is disclosed in PCT/GB00/00771. This describes a process for preparing a conjugated polymer, which comprises polymerising in a reaction mixture (a) an aromatic monomer having at least two boron derivative functional groups selected from a boronic acid group, a boronic ester group and a borane group, and an aromatic monomer having at least two reactive halide functional groups; or (b) an aromatic monomer having one reactive halide functional group and one boron derivative functional group selected from a boronic acid group, a boronic ester group and a borane group, wherein the reaction mixture comprises a catalytic amount of a catalyst suitable for catalysing the polymerisation of the aromatic monomers, and an organic base in an amount sufficient to convert the boron derivative functional groups into —BX$_3$ anionic groups, wherein X is independently selected from the group consisting of F and OH.

Another polymerisation method is disclosed in U.S. Pat. No. 5,777,070. Commonly, this process is known as "Suzuki Polymerisation". The process involves contacting monomers having two reactive groups selected from boronic acid, C1–C6 boronic acid ester, C1–C6 borane and combinations thereof with aromatic dihalide functional monomers or monomers having one reactive boronic acid, boronic acid, boranic acid ester or boring group and one reactive halide functional group with each other.

A further polymerisation method is known from "Macromolecules", 31, 1099–1103 (1998). The polymerisation reaction involves nickel-mediated coupling of dibromide monomers. This method commonly is known as "Yamamoto Polymerisation".

The present invention also provides a monomer for use in a polymerisation reaction comprising one or more reactive groups and a repeat unit as defined in any aspect above. Preferred reactive groups include halide or reactive boron derivatives groups. In particular, bromine, boronic acid, boronic ester and borane groups are preferred.

There are a number of approaches for the preparation of a monomer according to the present invention comprising an ortho-bis(triaryl)amine group. Firstly, the monomer could be prepared by reduction or hydrolysis of dibromo-benzothiadiazole followed by coupling to the diamine of various aromatic species using metal catalysed couplings for example, the modified Ullmann reaction. Such a reaction scheme is shown below:

Sheme 1.
General synthesis of ortho-bis triaryl amine units

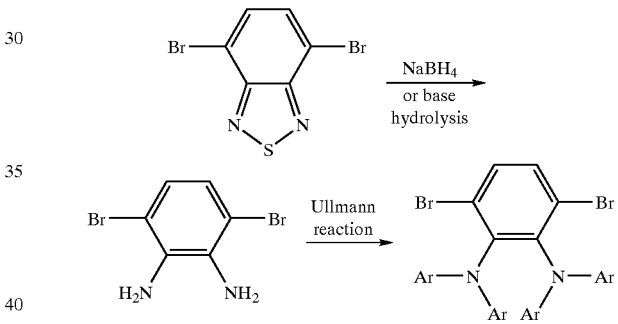

This monomer then can be incorporated into a conjugated polymer as shown below:

Sheme 2.
Metal catalysed polymerisation

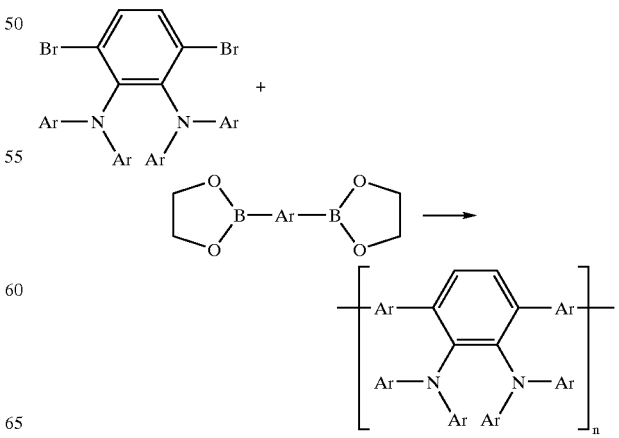

In addition to the monomers disclosed above, a further monomer in accordance with the present invention is:

A general reaction scheme for the preparation of this monomer is shown below:

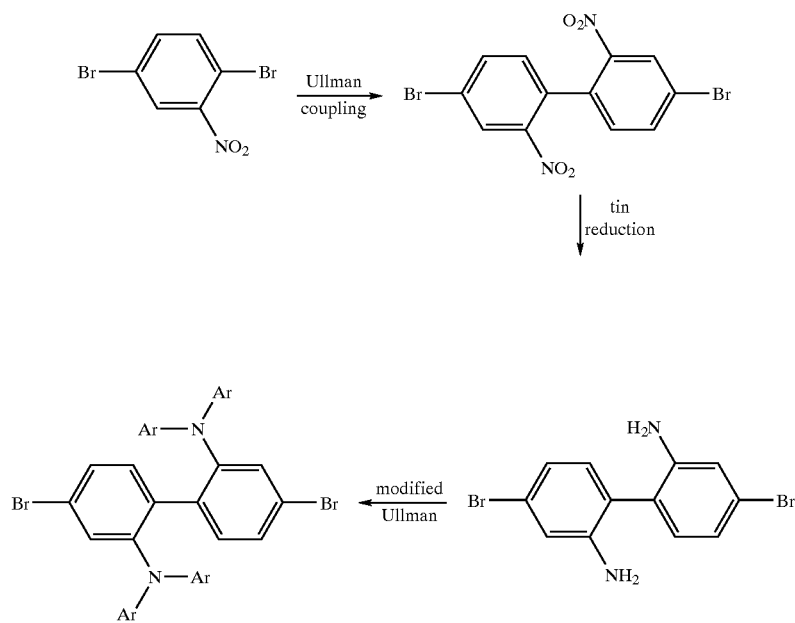

This product may be Stille coupled to a heterocyclic tin derivative to give a desired trimer unit, for example:

The monomer then can be incorporated into a conjugated polymer as shown below:

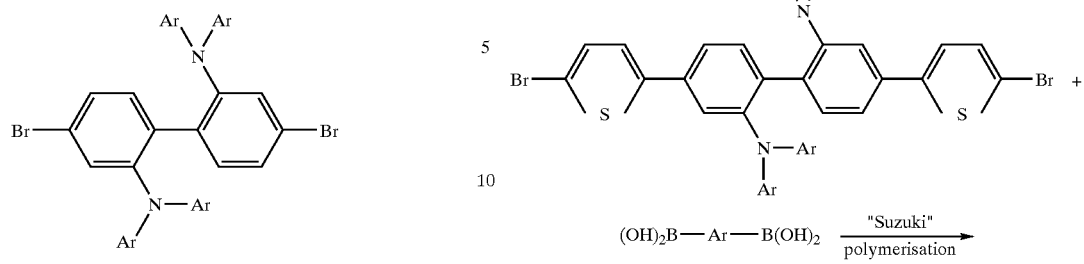

-continued $x = 98-40\%$
$y = 2-60\%$

Further reaction schemes for the preparation of monomers according to the present invention are shown below:

General scheme to orthotriarylamines

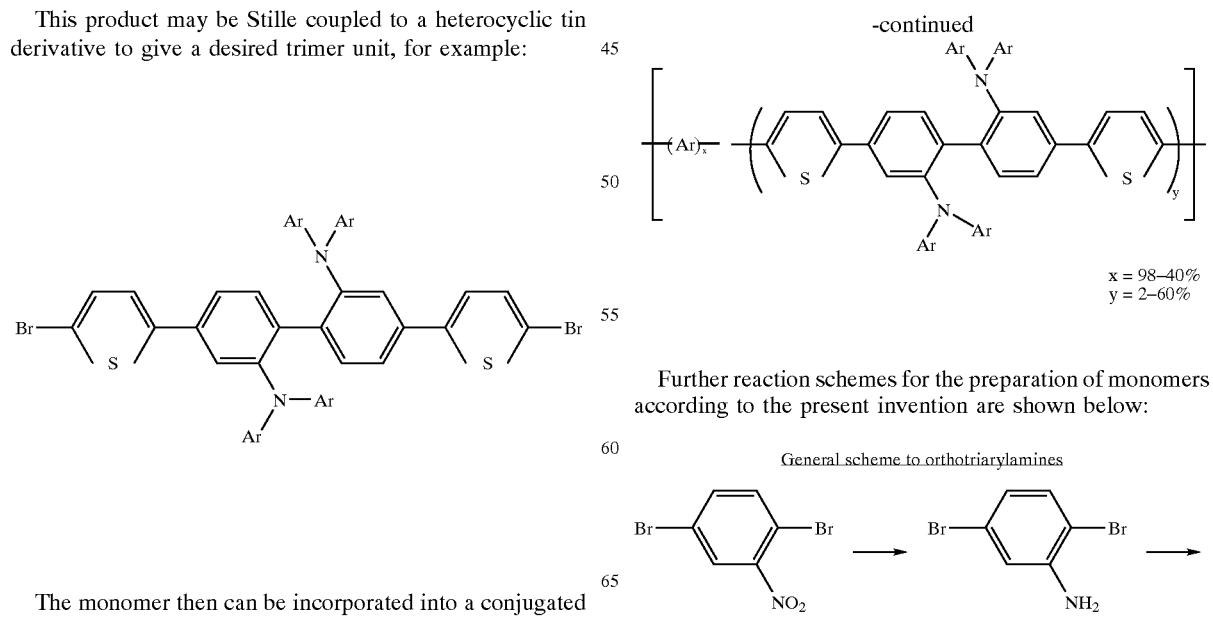

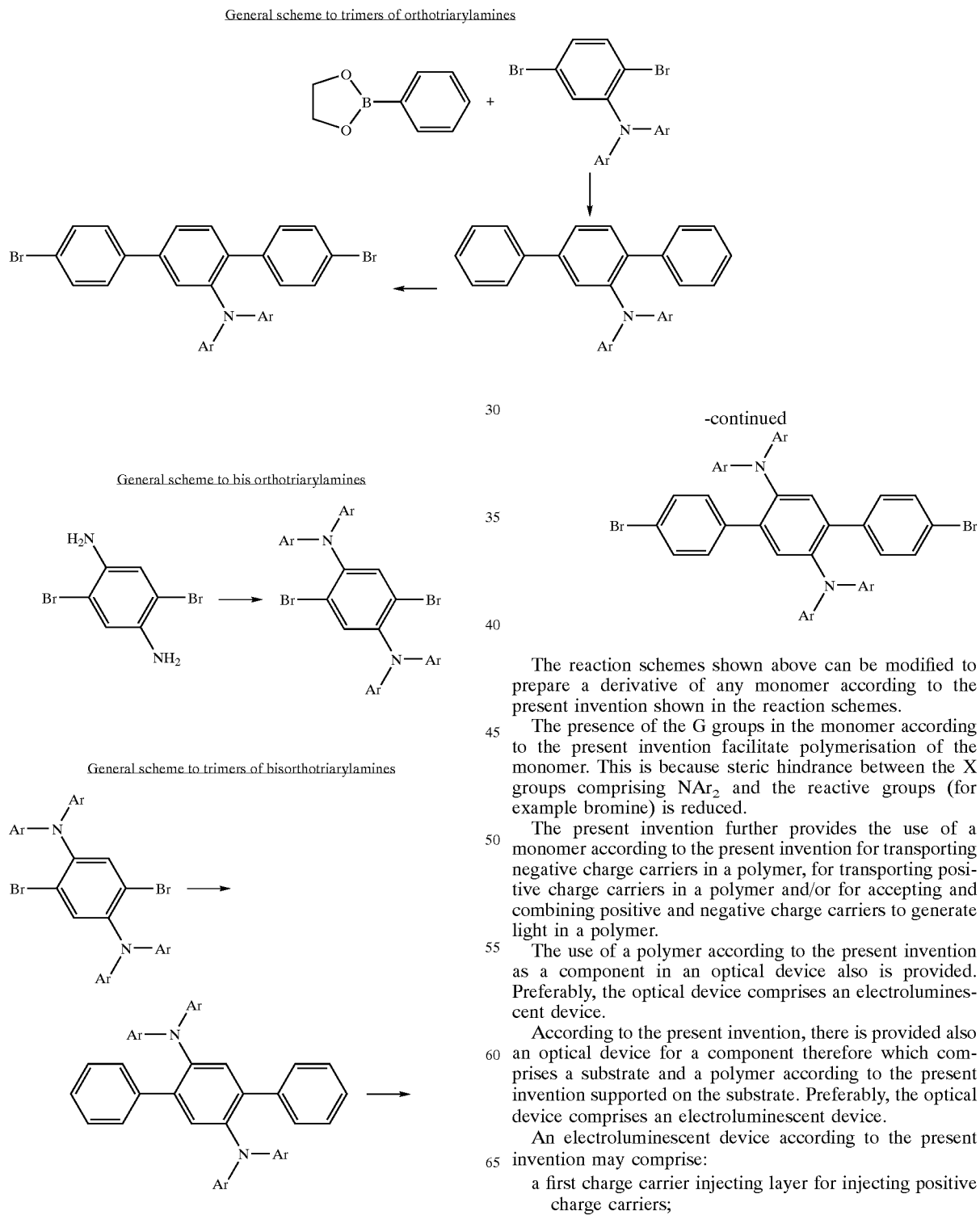

The reaction schemes shown above can be modified to prepare a derivative of any monomer according to the present invention shown in the reaction schemes.

The presence of the G groups in the monomer according to the present invention facilitate polymerisation of the monomer. This is because steric hindrance between the X groups comprising $NAr_2$ and the reactive groups (for example bromine) is reduced.

The present invention further provides the use of a monomer according to the present invention for transporting negative charge carriers in a polymer, for transporting positive charge carriers in a polymer and/or for accepting and combining positive and negative charge carriers to generate light in a polymer.

The use of a polymer according to the present invention as a component in an optical device also is provided. Preferably, the optical device comprises an electroluminescent device.

According to the present invention, there is provided also an optical device for a component therefore which comprises a substrate and a polymer according to the present invention supported on the substrate. Preferably, the optical device comprises an electroluminescent device.

An electroluminescent device according to the present invention may comprise:

a first charge carrier injecting layer for injecting positive charge carriers;

a second charge carrier injecting layer for injecting negative charge carriers;

a light-emissive layer located between the charge carrier injecting layers for accepting and combining positive and negative charge carriers to generate light; and a polymer according to the present invention for transporting negative charge carriers and optionally (a) for transporting positive charge carriers and/or (b) for combining positive and negative charge carriers to generate light and either located between the second charge carrier injecting layer and the light-emissive layer or located in the light-emissive layer.

Finally, the present invention provides a process for preparing a polymer according to the present invention comprising a step of reacting a first monomer which is a monomer according to the present invention with a second monomer that may the same or different from the first monomer under conditions so as polymerise the monomers. Such conditions will be well known to a person skilled in this art.

The present invention now will be described in more detail:

EXAMPLES

Example 1

Preparation of Dibromo Nitrobenzene

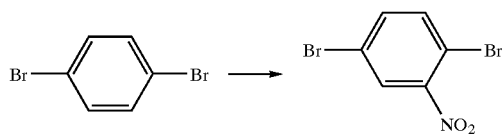

A cooled (−10° C.) solution of $H_2SO_4$ (200 mL) was treated with finely ground 1,4-dibromo benzene (94.2 g). the suspension was kept below 10° C. on addition of a cooled solution of (H2SO4/HNO3; 100:160 mL). The reaction mixture was allowed to warm to r.t. with stirring. After 24 h the reaction was quenched by pouring the suspension onto ice. The product precipitated out and was collected by filtration. The solid product was then vigorously stirred in water (twice) after which the product was filtered and air dried to afford 91.3 g (82%). Recrystallisation from methanol was carried out, normal purity after 1 recrystallisation is >98% by HPLC; $^1$H NMR (CDCl$_3$) 7.99 (1H, d, J 2.4), 7.62 (1H, d, J 8.4), 7.57 (1H, dd, J 8.8, 2.0), Ref: J.A.C.S, 1994, 116, 11723.

Example 2

Preparation of Dibromo Aniline

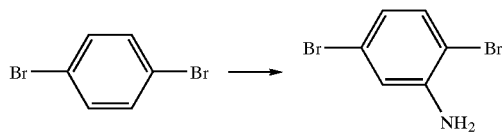

2,5-dibromo nitrobenzene (53.7 g, 24.9 mmol) in EtOH (180 mL) was added slowly (over 0.5 h) to a solution of tin (II) chloride dihydrate (327 g) in cHCl (272 mL). The reaction exotherms to ~60° C. after the addition is complete and then subsides. Stirring is continued for a further 18 h and then the product is filtered off. The crude solid is then suspended in EtOH (95%) and treated with NaOH 50% (250 mL) and vigorous stirring is continued for 30 mins. The product is then filtered off, washed with NaOH 50% (2×100 mL) and allowed to air dry giving 28.86 g (60% yield); $^1$H NMR (CDCl$_3$) 7.24 (1H, d, J 8.8), 6.89 (1H, d, J 2.0), 6.73 (1H, dd, J 8.4, 2.4), 4.05 (2H, brs); $^{13}$C NMR (CDCl$_3$) 107.968, 118.345, 121.966, 122.378, 133.837, 145.517. Ref: J.A.C.S, 1994, 116, 11723.

Example 3

Preparation of Amine 1 via the Modified Ullmann

A suspension of copper chloride (549 mg, 10%) and 1,10-phenanthroline

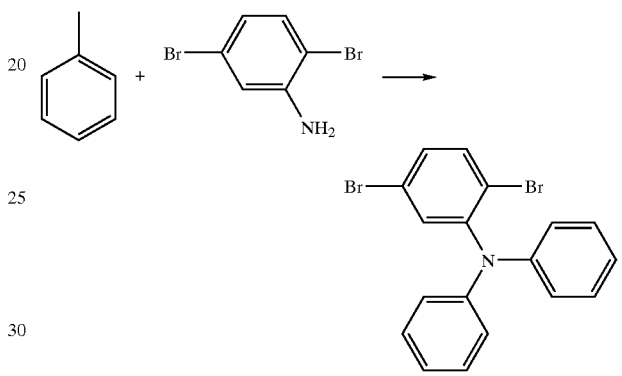

(1.0 g, 10%) in toluene (250 mL) was heated to 130° C. After 0.5 h, iodobenzene (22 mL, 196.5 mmol), 2, 2-dibromo aniline (13.9 g, 55.7 mmol) and flaked KOH (21.9 g, 547.5 mmol) was added to the solution and heating resumed at ~170° C. for 26 h. It was noted that the temperature rose to 185° C. for the last hour. Monitoring by GC_MS revealed de-bromination of product was observed. A standard aqueous work-up, followed by column chromatography (eluting with hexane) and finally recrystalisation from from IPA/Acetone gave 2.58 g (11% yield; 99.9% by HPLC); $^1$H nmr (CDCl$_3$) 7.49 (1H,d, J 8.8), 7.34 (1H,d, J 2.4), 7.26–7.19 (5H,m), 7.00 (2H, t, J 7.6), 6.97 (4H,t, J 7.2);

Example 4

Preparation of F8Amine 1 Protocol

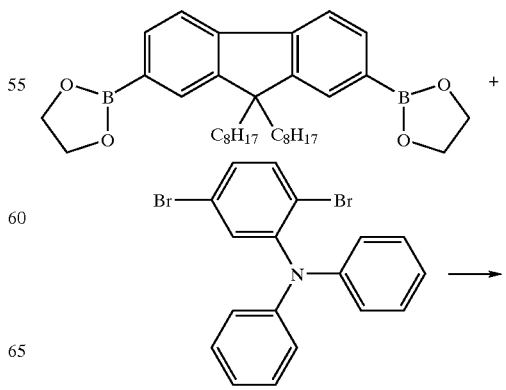

-continued

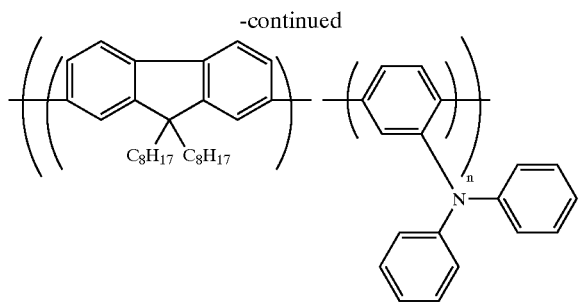

A suspension of F8-diester (4.46 g, 8.4 mmol), Amine 1 (3.39 g, 8.4 mmol) and tetrakis (triphenyl phosphine) palladium (0) (29 mg) in toluene (42 mL) was de-gased with nitrogen. After 0.5 h, tetraethyl ammonium hydroxide (28 mL) was added to the reaction mixture and the suspension heated to ~115° C. (external temp.). The reaction was end-capped with bromobenzene (1 mL) after 24 h. Stirring was maintained at 115° C. for 1 h then phenyl boronic acid (1.5 g) was added and stirring continued for a further 1.5 h. Once the reaction mixture had cooled to r.t. the polymer was precipitated into methanol (3 L). The polymer was filtered off and re-dissolved in toluene (250 mL). A solution of dithiocarbamic acid (30 g) in H₂O (120 mL) was added to the toluene solution. The salt mixture was heat to 65° C. for 18 h and then the aqueous layer was removed. The organic phase was passed down an alumina/silica column, eluting the polymer with toluene. The toluene was condensed to 250 mL and then precipitated into methanol (4L). The polymer was filtered off and dried thoroughly affording 3.81 g; Mp 80,000.

Example 5

An Optical Device

A suitable device structure is shown in FIG. 1. The anode 2 is a layer of transparent indium-tin oxide ("ITO") supported on a glass or plastic substrate 1. The anode 2 layer has a thickness between 1000–2000 Å, usually about 1500 Å. The cathode 5 is a Ca layer having an approximate thickness of 1500 Å. Between the electrodes is a light emissive layer 4 having a thickness up to about 1000 Å. The emissive layer 4, for example, comprises between 0.5 to 30% by weight of the present polymer with the remainder of the emissive layer consisting of hole transport material and/or emissive material. Advantageously, the device includes a hole transport material layer 3 of PEDOT having a thickness of about 1000 Å. Layer 6 is an encapsulant layer of a suitable thickness.

What is claimed is:

1. A polymer capable of transporting negative charge carriers comprising a region having a conjugated backbone consisting of repeat units selected from the group consisting of aromatic groups and heteroaromatic groups, wherein at least one of said aromatic groups or heteroaromatic groups is a core group |Ar'| substituted with at least one pendant group X, wherein each X comprises NAr₂ in which each Ar is the same or different and independently comprises a substituted or unsubstituted aromatic or heteroaromatic group and N is conjugated with the backbone.

2. A polymer according to claim 1, wherein each Ar comprises a substituted or unsubstituted aryl or heteroaryl group.

3. A polymer according to claim 2, wherein each Ar comprises at least one phenyl or pyridyl group.

4. A polymer according to claim 1, wherein the Ar groups in NAr₂ are the same.

5. A polymer according to claim 1, wherein Ar' is a phenyl group.

6. A polymer according to claim 1, wherein each core group has the formula:

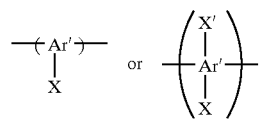

wherein X and X' are the same or different and each is as X is defined in claim 1.

7. A polymer according to claim 6, wherein each core group has the formula:

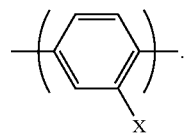

8. A polymer according to claim 7, wherein each core group has the formula:

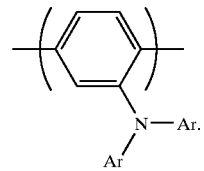

9. A polymer according to claim 6, where X and X' are ortho or para to one another.

10. A polymer according to claim 9, wherein each core group has the formula:

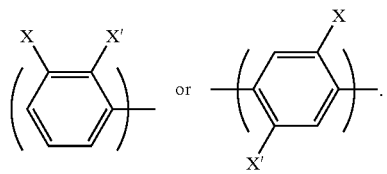

11. A polymer according to claim 10, wherein each core group has the formula:

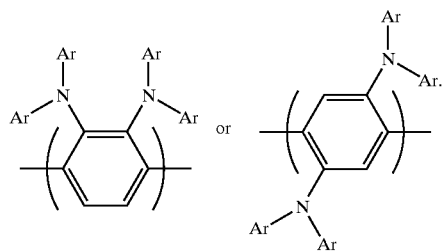

12. A polymer according to claim 1, wherein each core group has the formula:

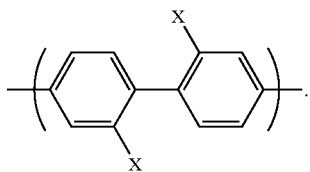

13. A polymer according to claim 12, wherein each core group has the formula:

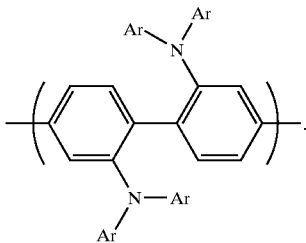

14. A polymer according to claim 1, wherein the repeat unit further comprises one or more groups G where each G is the same or different and independently comprises a substituted or unsubstituted aromatic or heteroaromatic group so that the repeat unit has a formula:

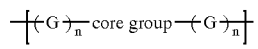

where $0 \leq n \leq 2$.

15. A polymer according to claim 14, where G is phenyl, thienyl or pyridyl.

16. A polymer according to claim 15, wherein G is thienyl.

17. A polymer according to claim 14, where n=1.

18. A polymer according to claim 1, comprising a copolymer.

19. A monomer for use in a polymerisation reaction, comprising one or more reactive groups and a monomeric unit having the structure of a repeat unit as defined in claim 1.

20. A process for preparing a polymer comprising a step of reacting a first monomer as defined in claim 19 with a second monomer that may be the same or different from the first monomer under conditions so as to polymerise the monomers.

21. An optical device or a component therefore, which comprises a substrate and a polymer according to claim 1 supported on the substrate.

22. A polymer comprising a region having a conjugated backbone capable of transporting negative charge carriers, which region comprises a plurality of repeat units each comprising a core group which forms at least a part of the backbone, wherein each core group has the formula:

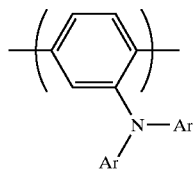

wherein each X comprises NAr$_2$ in which each Ar is the same or different and independently comprises a substituted or unsubstituted aromatic or heteroaromatic group and N is conjugated with the backbone.

23. A polymer comprising a region having a conjugated backbone capable of transporting negative charge carriers, which region comprises a plurality of repeat units each comprising a core group which forms at least a part of the backbone, wherein each core group has the formula:

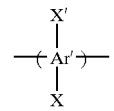

wherein Ar' comprises an aromatic or heteroaromatic group;

X and X' are ortho to one another, are the same or different, and each comprises NAr$_2$ in which each Ar is the same or different and independently comprises a substituted or unsubstituted aromatic or heteroaromatic group; and, N is conjugated with the backbone.

24. A polymer according to claim 23, wherein each core group has the formula:

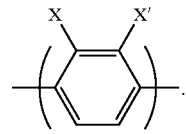

25. A polymer according to claim 24, wherein each core group has the formula:

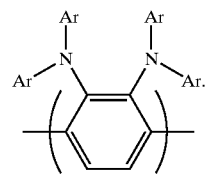

26. A polymer comprising a region having a conjugated backbone capable of transporting negative charge carriers, which region comprises a plurality of repeat units each comprising a core group which forms at least a part of the backbone, wherein each core group has the formula:

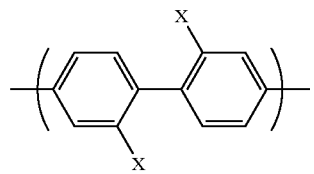

wherein each X comprises NAr$_2$ in which each Ar is the same or different and independently comprises a substituted or unsubstituted aromatic or heteroaromatic group and N is conjugated with the backbone.

27. A polymer according to claim 26, wherein each core group has the formula:

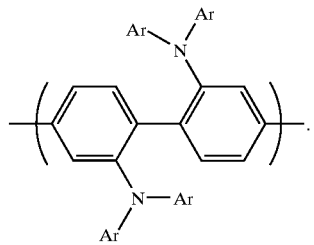

* * * * *